(12) United States Patent
Kelly

(10) Patent No.: US 6,340,703 B1
(45) Date of Patent: *Jan. 22, 2002

(54) TREATMENT OR PREVENTION OF OSTEOPOROSIS

(75) Inventor: Graham E. Kelly, Northbridge (AU)

(73) Assignee: Novogen, Inc., Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,590
(22) PCT Filed: May 1, 1998
(86) PCT No.: PCT/AU98/00313
§ 371 Date: Jun. 2, 1998
§ 102(e) Date: Jun. 2, 1998
(87) PCT Pub. No.: WO98/50026
PCT Pub. Date: Nov. 12, 1998

(30) Foreign Application Priority Data

May 1, 1997 (AU) .............................................. PO6568
Dec. 8, 1997 (AU) .............................................. PP0814

(51) Int. Cl.$^7$ ........................ A61K 31/352; A61P 19/10
(52) U.S. Cl. ...................................... 514/456; 514/899
(58) Field of Search ................................ 514/456, 899

(56) References Cited

U.S. PATENT DOCUMENTS

| | | | |
|---|---|---|---|
| 4,390,559 A | | 6/1983 | Zilliken |
| 5,141,746 A | | 8/1992 | Fleury et al. |
| 5,424,331 A | * | 6/1995 | Shlyankevich ............... 514/456 |
| 5,498,631 A | * | 3/1996 | Gorbach et al. ............ 514/456 |

FOREIGN PATENT DOCUMENTS

| | | |
|---|---|---|
| AU | A-24813/97 | 6/1997 |
| EP | 0426998 A2 | 5/1991 |
| JP | 61246124 A | 11/1986 |
| JP | 62126186 A | 6/1987 |
| JP | 01258669 A | 10/1989 |
| JP | 02069165 A | 3/1990 |
| JP | 03047049 A | 2/1991 |
| WO | WO93/23069 | 11/1993 |
| WO | WO94/23716 | 10/1994 |

OTHER PUBLICATIONS

U.S. application No. 08/049,006, filed 1993, Gorbach et al.

Adlercreutz, H. et al., "Determination of Urinary Lignans and Phytoestrogen Metabolites, Potential Antiestrogens and Anticarcinogens, in Urine of Women on Varios Habitual Diets," *J. Steroid Biochem*, vol. 25, No. 58, pp. 791–797 (1986).

Adlercreutz, Herman et al., "Dietary Phytoestrogens and Cancer in Vitro and in Vivo Studies," *J. Steroid Biochem Molec. Bio.*, vol. 41, No. 3–8 pp. 331–337 (1992).

Adlercreutz, Herman et al., "Dietary phyto–oestrogens and the menopause in Japan," *The Lancet*, pp. 1233 (1992).

Adlercreutz, H. et al., "Excretion of the Lignans Exterolactone and Enterodiol and of Equol in Omnivorous and Vegetarian Postmenopausal Women and in Women with Breast Cancer," *The Lancet*, pp. 1295–1299 (1982).

Adlercreutz, H. et al., "Lignans and Phytoesrogens", *Front. gastrointest. Res.*, vol. 14, pp. 165–176 (1988).

Adlercreutz, Herman et al., "Urinary Excretion of Lignans and Isoflavonoids Phytoestrogens in Japanese Men and Women Consuming a Traditional Japanese Diet," *Am. J. Clin. Nutr.*, vol. 54, pp. 1093–1100 (1991).

Adlercreutz, Herman, "Western Diet and Wester Diseases: Some Hormonal and Biochemical Mechanisms and Associates," *Scand. J. Clin. Lab. Invest*, Suppl., vol. 201 pp. 3–23 (1990).

Anderson M.D., James et al., "Meta–Analysis of the Effects of Soy Protein Intake on Serum Lipids," *New Eng. J. Med.*, vol. 333, No. 5, pp. 276–282 (1995).

Barnes, Stephen et al., "Soybeans Inhibit Mammary Tumors in Models of Breast Cancer," *Mutagens and Carcinogens in the Diet*, pp. 239–253 (1990).

Bailey, E.T. et al., "Isoflavone Concentration in the Leaves of the Species of the Genus *Trifolium*, Section *Calycomorphum*," *Aust. J. Agric. Res.*, vol. 22, pp. 731–736 (1971).

Bannwart, Christoph et al., "Identification of the Isoflavonic Phytoestrogen daidzein in Human Urine," *Clinica Chimica Acta*, vol. 136, pp. 165–172 (1984).

Barrow, N.J. et al., "Nutrient Potential and Capacity," *Aust. J. Agric. Res.*, vol. 17, pp. 849–861 (1966).

Barrow, N.J. et al., "Nutrient Potential and Capacity" (1966).

Beck, A.B., "The Oestrogenic Isoflavones of Subterranean Clover," *Aust. J. Agric. Res.* (1964).

(List continued on next page.)

*Primary Examiner*—Edward J. Webman
(74) *Attorney, Agent, or Firm*—Finnegan, Henderson, Farabow, Garrett, & Dunner, L.L.P.

(57) ABSTRACT

There is described a method for the treatment or prevention of menopausal symptoms or osteoporosis wherein there is administered to a subject in need of such treatment a therapeutically effective amount of the isoflavone formononetin, or a method for the treatment or prevention of menopausal symptoms wherein there is administered to a subject in need of such treatment a therapeutically effective amount of the isoflavone daidzein, the isoflavone being optionally administered with one or more pharmaceutically acceptable adjuvants, carriers and/or excipients. Therapeutic uses and compositions/foods are also described, comprising daidzeii or formononetin optionally in association with one or more pharmaceutically acceptable adjuvants, carriers, food components and/or excipients.

19 Claims, No Drawings

OTHER PUBLICATIONS

Beckham, N., "Menopause," *The Family Guide to Natural Therapies*, Greenhouse Publications, pp. 41–42, 50 (1988).

Beckham, Nancy, "Herbal Help to Avoid Menopause Symptons," *Australian Wellbeing*, No. 29, pp. 74–76 (1988).

Beckham, Nancy, "Phyto–Oestrogens and Compounds that Affect Oestrogen Metabolism—Part I," *Aust. J. Med. Herbalism*, vol. 7, No. 1, pp. 11–16 (1995).

Beckham, Nancy, "Phyto–Oestrogens and Compounds that Affect Oestrogen Metabolism—Part II," *Aust. J. Med. Herbalism*, vol. 7, No. 2, pp. 27–33 (1995).

Bennetts, H.W. et al., "A Specific Breeding Problem of Sheep on Subterranean Clover Pastures in Western Australia," *The Australian Veterinary Journal*, vol. 22, pp. 2–12 (1946).

Beuker Velesse—Advertising Brochure—with English language translation.

Bombardelli, Ezio, "Technologies for the Processing of Medicinal Plants," in *The Medicine Plant Industry*, Chapt. 7, pp. 85–98 (1991).

Bradbury, R.B. et al., "The Chemistry of Subterranean Clover. Part I. Isolation of Formonoetin and Genistein," *J. Chem. Soc.*, pp. 3447–3449 (1951).

Bradbury, R.B. et al., "Estrogens and Related Substances in Plants," in *Vitamins and Hormones Advances in Research and Applications*, Harris, R.S. et al., eds., pp. 207–233 (1954).

Brandi, M.L., "Flavonoids: biochemical effects and therapeutic applications," *Bone and Mineral*, vol. 19 (Suppl.) S3–S14 (1992).

Braden, A.W.H. et al., "Comparison of Plasma Phyto–Oestrogen Levels in Sheep and Cattle After Feeding on Fresh Clover," *Aust. J. Agric. Res.*, vol. 22, pp. 663–70 (1971).

Braden, A.W.H. et al., "The Oestrogenic Activity and Metabolism of Certain Isoflavones in Sheep," *Aust. J. Agric. Res.*, vol. 18 pp. 335–48 (1967).

Circle, S. J. et al., "Processing Soy Flours, Protein Concentrates and Protein Isolates," *Soybeans: Chemistry and Technology*, vol. 1, pp. 294–338 (1972).

Coward, Lori et al., "Genistein, Daidzein, and Their β–Glycoside Conjugates: Antitumor Isoflavones in Soybean Foods from American and Asian Diets," *J. Agric. Food Chem.*, vol. 41, pp. 1961–67 (1993).

Culbreth, Lloyd H. et al., "Further Studies on Oestrogenic Activity in Strains of Subterranean Clober (*Trifolium Subterranean L.*) In South–Western Australia," *Aust. J. Agric. Res.* (1965).

Davis, Harold et al., "Extraction," *Bentleys's Text–Book of Pharmaceuticals*, 6th ed., XVIII, pp. 272–273 (1956).

Düker, Eva–Maria et al., "Effects of Extracts from *Clinifuga Racemosa* on Gonadotropin Release in Menopausal Women and Ovariectomized Rats," *Planta Med.*, vol. 57, pp. 420–424 (1991).

Eldridge, Arthur C., "Determination of Isoflavones in Soybean Flours, Protein Concentrates, and Isolates," *J. Agric. Food. Chem.*, vol. 30, pp. 353–355 (1982).

Eldridge, A.C., "High–performance liquid chromatography separation of soybean iso–flavones and their glucosides," *J. Chrom.*, vol. 234 pp. 494–496 (1982).

Eldridge, Arthur C., "Soybean Isoflavones: Effect of Environment and Variety on Composition," *J. Agric. Food Chem.*, vol. 31 pp. 394–96 (1983).

Farmakalidis, Efi et al., "Isolation of 6"–O–Acetylgenistin and 6"–O–Acetyldaidzin from Toasted Defatted Soyflakes," *J. Agric. Food Chem.*, vol. 33, pp. 385–389 (1985).

Farmakalidis et al., "Semi–Preparative High–Performance Liquid Chromatographic Isolation Soybean Isoflavones," *J. Chrom.*, vol. 295, pp. 510–514 (1984).

Farnsworth, Norman R., "Potential Value of Plants as Sources of New Antifertility Agents II," *J. Pharm. Sciences*, vol. 64, No. 5, pp. 717–754 (1975).

Francis, C.M. et al., "The Distribution of Oestrogenic Isoflavones in the Genus Trifolium," *Aust. J. Agric. Res.* (1966).

Francis, C.M. et al., "Varietal Variation in the Isoflavone Content of Subterranean Clover: Its Estimation by a Microtechnique," *Aust. J. Agric. Res.* (1965).

Gildersleeve, Rhonda R. et al., "Screening Rose Clover and Subterranean Clover Germplasm for Isoflavones," *Crop. Sci.*, vol. 31 pp. 1374–1376 (1991).

Gildersleeve, Rhonda R. et al., "Detection of Isoflavones in Seedling Subterranean Clover," *Crop. Sci.*, vol. 31, pp. 889–892 (1991).

Gladstones, J.S., "Naturalized Subterranean Clover Strains in Western Australia: A Preliminary Agronomic Examination," *Aust. J. Agric. Res.*, vol. 8, pp. 713–731 (1967).

Herman, C. et al., "Soybean Phytoestrogen Intake and Cancer Risk," *American Institute of Nutrition*, pp. 7575–7705 (1995).

Holt, S., "Selected Bibliography of Scientific Studies on Genistein and Other Soya Isoflavones," Soya for Health: *The Definitive Medical Guide*, pp. 159–170 (1996).

Jenkins, David J.A. et al., "Leguminous seeds in the dietary management of hyperlipidemia$^{1-3}$," *Am. J. Clin. Nut.*, vol. 38, pp. 567–573 (1983).

Jones, Amanda E. et al., "Developement and Application of a High–Performance Liquid Chromatographic Method for the Analysis of Phytoestrogens," *J. Sci. Food Agric.*, vol. 46, pp. 357–364 (1989).

Kaidas, Rami S. et al., "Reproductive and General Metabolic Effects of Phytoestrogens in Mammals," *Reproductive Toxicology Review*, vol. 3, No. 2, pp. 81–89 (1989).

Kitada, Yoshimi et al., "Determination of Isoflavones in soy bean by high–performance liquid chromatography with amperometric detection," *J. Chrom.*, vol. 366, pp. 403–406 (1986).

Knuckles, Benny E. et al., "Coumestrol Content of Fractions Obtained During West Processing of Alfalfa," *J. Agric. Food Chem.*, vol. 24, No. 6, pp. 1177–1180, (1976).

Kudou, Shigemitsu et al., "A New Isoflavone Glycoside in Soybean Seeds (*Glycine max* Merrill), Glycitein 7–O–β–D–(6'–O–Acetyl)–Glucopyranoside," *Agric. Biol. Chem.*, vol. 55, No. 3, pp. 859–860 (1991).

Kudou, Shigemitsu et al., "Malonyl Isoflavone Glycosides in Soybean Seeds (*Glycine max* Merrill)," *Agric. Biol. Chem.*, vol. 55, No. 9, pp. 2227–2233 (1991).

Lindner, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–33 (1967).

Lock, Margaret, "Contested meanings of the menopause," *The Lancet*, vol. 337, pp. 1270–1272 (1991).

Martin, P.M. et al., "Phytoestrogen Interaction with Estrogen Receptors in Human Breast Cancer Cells," *Endocrinology*, vol. 193, No. 5, pp. 1860–1867 (1978).

Messina, Mark et al., "The Role of Soy Products in Reducing Risk of Cancer," *J. of National Cancer Institute*, vol. 83, No. 8, pp. 541–546 (1991).

Morris, P., "Identification and Accumulation of Isoflavonoids and Isoflavone Glucosides in Soybean Leaves and Hypocotyls in Resistance Responses to Phytophthora *Megaspermas f.sp. Glycinea*," *Physiological and Molecular Plant Pathology*, 39, pp. 221–244 (1991).

Murphy, P.A., Phytoestrogen Content of Processed Soybean Products, *Food Technology*, pp. 60–64 (1982).

Murphy, P.A., "Separation of Genistin, Daidzin and Their Aglucones, and Coumesterol by Gradient High Performance Liquid Chromatography," *J. Chrom*, vol. 211, pp. 166–169 (1991).

Naim, M. et al., "A New Isoflavone from Soya Beans," *Phytochemistry*, vol. 12, pp. 169–170 (1973).

Naim, M. et al., "Soybean Isoflavones, Characterization, Determination, and Antifungal Activity," *J. Agric. Food Chem.*, vol. 22, No. 5, pp. 806–810 (1974).

Nash, A.M. et al., "Fractionation and Characterization of Alcohol Extractables Associated with Soybean Proteins, Nonprotein Components," *J. Agric. Food Chem.*, vol. 15, No. 1, pp. 102–108 (1967).

Ohta, Naokazu et al., "Isoflavonoid Constituents of Soybeans and Isolation of a New Acetyl Daidzin," *Agric. Biol. Chem.*, 43, vol. No. 7, pp. 1415–1419 (1979).

Okano, Koji et al., "Isolation of Four Kinds of Isoflavon from Soya Bean," *Bron: Bull. Agric. Chem. Soc. Japan*. 15, vol. 15, p. 110 (1939).

Okubo, Kazuyoshi et al., "Components Responsible for the Undesirable Taste of Soybean Seeds," *Biosci. Biotech. Biochem.*, vol. 56, No. 1, pp. 99–103 (1992).

Pope, G.S., "The importance of Pasture Plant Oestrogens in the Reproduction of Lactation of Grazing Animals," *Dairy Science Abstracts*, vol. 16, No. 5, pp. 333–356 (1954).

Price, K.R. et al., "Naturally Occurring Oestrogens in Foods—A Review," *Food Additives and Contaminants*, vol. 2, No. 2 pp. 73–106 (1985).

Reinli, Kathrin et al., "Phytoestrogen Content of Foods—A Compendium of Literature Values," *Nutrition and Cancer*, vol. 26, No. 2, pp. 123–148 (1996).

Rose, David P., "Dietary Fiber, Phytoestrogens, and Breast Cancer," *Nutrition*, vol. 8, No. 1 (1992).

Rossiter, R.C., "Physiological and Ecological Studies on the Oestrogenic Isoflavones in Subterranean Clober (T. *Subterraneum L.*" *Aust. J. Agric. Res.*, Chapter III (1966).

Rossiter, R.C., "Physiological and Ecological Studies on the Oestrogenic Isoflavones in *Subterranean clober* (T. *Subterraneum L.*)" *Aust. J. Agric. Res.*, Chapter IV (1966).

Seo, A. et al., "Improved High–Performance Liquid Chromatographic Analysis of Phenolic Acids and Isoflavonoids from Soybean Protein Products," *J. Agric. Food Chem.*, vol. 32 No. 3, pp. 530–533 (1984).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chrom.*, vol. 386 pp. 315–323 (1987).

Setchell, K.D.R. et al., "Mammalian Lignans and Phyto–oestrogens Recent Studies on their Formation, Metabolism and Biological Role in Health and Disease," in Role of the Gut Flora in Toxicity and Cancer, pp. 315–339 (1988).

Setchell, KDR et al., "Nonsteroidal estrogens of dietary origin: possible roles in hormone–dependent disease," *Am. J. Clin. Nut.*, vol. 40 pp. 569–578 (1984).

Shimoyamada, Makoto et al., "Saponin Composition in Developing Soybean Seed (Glycine max (L.) Merrill, cv. Mikuriyaao)," *Agric. Biol. Chem.*, vol. 55, No. 5, pp. 1403–1405 (1991).

Shutt, Donald A., "The Effects of Plant Oestrogens on Animal Reproduction," *Endeavour*, vol. 35, pp. 110–113 (1976).

Shutt, D.A. et al., "Free and Conjugated Isoflavones in the Plasma of Sheep Followed Ingestion of Oestrogenic Clover," *Aust. J. Agric. Res.*, vol. 18 pp. 647–55 (1967).

Shutt, D.A., "Interaction of Genistein With Oestradiol in the Reproductive Tract of the Ovariectomized Mouse," *J. Endrocrin.*, vol. 37, pp. 231–232 (1967).

Shutt, D.A. et al., "Quantitative Aspects of Phyto–Oestrogen Metabolism in Sheep Fed on Subterranean Clover (*Trifolium Subterraneum*) Cultivar Clare) or Red Clover (Trifolium Pratense)," *Aust. J. Agric. Res.*, vol. 21, pp. 713–22 (1970).

Shutt, D.A. et al., "The Significance of Equol in Relation of the Oestrogenic Responses in Sheep Ingesting Clover With a High Formononetin Content," *Aust. J. Agric. Res.*, vol. 19, pp. 545–53 (1968).

Shutt, D.A. et al., "Steroid and Phyto–Oestrogen Binding to Sheep Uterine Receptors In Vitro," *J. Endocr.*, vol. 52, pp. 299–310 (1972).

Smith, G.R. et al., "Influence of Harvest Date, Cultivar, and Sample Storage Method on Concentration of Isoflavones in Subterranean Clover," *Crop Science*, vol. 26 (1986).

Trease, G.E. et al., "Pharmacognosy," $12^{th}$ Ed., pp. 242–260 (1983).

Verdeal, Kathey et al., "Naturally–Occurring Estrogens in Plant Foodstuffs—A Review," *J. Food Protect.*, vol. 42, No. 7, pp. 577–583 (1979).

Walter, E.D., "Genistin (an Isoflavone Glucoside) and its Aglucone, Genistein, from Soybeans," *J. Am. Chem. Soc.*, vol. 63, p. 3273 (1941).

Walz, E., "Isoflavon–und Saponin–Glucoside in Soja hispida" *Justus Liebigs Ann. Chem.*, vol. 489, pp. 118–155 (1931).

Wang, G. et al., "A Simplified HPLC Method for Determination of Phytoestrogens in Soybean and Its Processed Products," *J. Agr. Food Chem.*, vol. 38, No. 1, pp. 185–190 (1990).

White, Edmund et al., "Extracta," *Pharmacopedia*, 2d ed. (1909).

Wilcox, G. et al., "Oestrogenic effects of plant foods in post–menopausal women," *British Med. J.*, vol. 301, pp. 905–906 (1995).

Wong, E., "Detection and Estimation of Oestrogenic Constituents in Red Clover," *J. Sci. Food Agric.*, vol. 13, pp. 304–308 (1962).

Wong, E., "The Oestrogenic Activity of Red Clover Isoflavones and Some of Their Degradation Products," *J. Endocrin.*, vol. 24, pp. 341–348 (1962).

"Estrogenic Activity in Plants," Brisbane Seminar (Summary of Talk by Nancy Beckham) (1985).

The Merck Index, Eighth Edition (1968).

"Phenolic Constituents," *Soybeans: Chemistry and Technology*, p. 149.

"Uterine Weight Changes and $^3$H–Uridine Uptake in Rats Treated with Phytoestrogens," *Can. J. Anim. Sci.*, vol. 60 pp. 531–534 (1980).

* cited by examiner

TREATMENT OR PREVENTION OF OSTEOPOROSIS

This invention relates to compositions, therapeutic uses and methods of treatment or prevention of menopausal symptoms and osteoporosis.

Menopausal symptoms and osteoporosis are significant scourges in the female population, generally affecting many women in later life.

Menopausal symptoms are very well known and are described, for example, by Greene, J. G. and Cooke, D. J. (1980) *British Journal of Psychiatry* Volume 136, 486–491 (incorporated herein by reference). Hot flushes are one of the principal menopausal symptoms which are uncomfortable and irritating. Greene and Cooke have developed a score in order to measure menopausal symptoms in women. This score is approved by the U.S. Department of Health and widely used in the medical community. The indicators of menopausal symptoms according to Greene and Cooke comprise hot flushes, sweating at night, heart beating quickly or strongly, feelings of tension or nervousness, difficulty in sleeping, excitability, attacks of panic, difficulties in concentrating, feelings of tiredness or lack of energy, unhappiness or depression, crying spells, irritability, feelings of dizziness or faintness, pressure or tightness in head or body, parts of the body feeling numb or tingling, dry vagina and/or dry mouth, headaches, muscle and joint pains, loss of feeling in hands or feet, breathing difficulties, and loss of interest in sex.

The peri-menopausal stage of life in women is associated with a fall in blood levels of the three major estrogens— estradiol, estrone and estriol—which occurs naturally in women usually between 45–55 years of age. The primary or acute menopause symptoms which effect menopausal women include hot flushes and night sweats. These are associated with often dramatically increased blood perfusion of the skin producing discomfort and sweating.

The precise mechanism of these symptoms is unknown but generally is thought to represent disturbance to normal homeostatic mechanisms controlling vasomotor activity and thermoregulation.

The fact that treatment and/or prevention with replacement estrogens usually relieves the symptoms (so-called estrogen replacement therapies) establishes the link between these symptoms and an estrogen deficiency. The menopausal stage of life is associated with a wide range of other acute symptoms as described above and these symptoms are generally estrogen-responsive.

Osteoporosis is believed to affect one third to one half of all post-menopausal women. In the United States it has been reported that annually 500,000 bone fractures occur as a result of osteoporosis. It is further reported that nearly one third of women over 65 will suffer at least one bone fracture resulting from osteoporotic bone weakening. Increased calcium intake and other approaches are suggested to have some effect. However, the widespread effects of osteoporosis indicates effective approaches for prevention/treatment have not yet arisen.

It has previously been thought that reduction in endogenous estrogen levels which occurs prior to menopause causes or contributes to the symptoms of menopause, as well as post-menopausal osteoporosis.

Isoflavones, being plant chemicals which occur largely in members of Leguminosae, display a range of biological functions which have suggested they may be useful in treating a host of medical conditions.

A small sub-group of isoflavones (comprising daidzein, genistein, biochanin, and formononetin and) is distinguished by their ability to bind to estrogen receptors on animal (including human) cells. This is due to the close similarity of the steric structure of the diphenolic rings of isoflavones with the steroidal ring structure of estrogens such as estradiol, estrone and estriol. Although having substantially lower binding affinity to the receptor compared to steroidal estrogens, estrogenic isoflavones are weakly estrogenic. This group of five isoflavones have the most basic diphenolic structure possible in contrast to the relatively more complex structures of other isoflavonoid compounds. This simplicity of structure and its close proximity in shape to the steroidal ring structure of estrogenic hormones is believed to grant these compounds their estrogenicity. This group also exhibits a range of biological functions in animal cells which appear to be independent of the estrogen receptor and these include anti-oxidant, diuretic, anti-spasmolytic and anti-cancer effects. These interesting functions with their potential therapeutic benefits has brought this particular group of isoflavones to the attention of medical researchers in recent years.

In the plant, the isoflavones can occur in a variety of forms—(i) in the basic form, (ii) in a malonyl form, and (iii) in an acetyl form; the isoflavones are biologically active in each of these forms. The naturally-occurring state for each of these forms is as a glycoside, being bound to a sugar moiety such as glucose to produce a water-soluble form. In this form, the isoflavone has enhanced stability to degradative factors such as heat, oxidation and ultraviolet irradiation. This water-soluble form also permits transport of the isoflavone both around the plant and intra-cellularly. At the intracellular site of biochemical function of the isoflavone, an intra-cellular glucoside enzyme cleaves the sugar moiety, leaving the more biologically active, but water-insoluble, aglucone form.

When ingested in the diet, the isoflavones undergo varying degrees of metabolism within the gut, within the gut wall, and within the liver before entering the parenteral bloodstream to exert their biological effects. The first metabolic process is the hydrolysis of the glucosidic form to the aglucone form. This occurs as a result both of low pH from gastric acid and of the action of β-glycosidase enzyme activity within bowel bacteria.

Some of the aglucone isoflavones are absorbed intact and in passing through the gut wall are believed to be glucuronated or sulphonated as per steroidal compounds. The bulk of isoflavones are fermented within colonic bacteria. One of the fermentation processes is to demethylate isoflavones (eg. formononetin gives daidzein and biochanin gives genistein on demethylation). In another series of fermentation steps, daidzein and genistein are converted to a range of end-products including equol, dehydroequol, O-desmethylangolensin (ODMA), 6-hydroxy-ODMA, 2-dehydro-ODMA, dihydrodaidzein, tetra-hydrodaidzein and dihydrogenistein. The liver is capable of further demethylation of isoflavones such as formononetin and biochanin to the more basic daidzein and genistein structures. The isoflavones and their metabolites and derivatives circulate freely within the body and are excreted primarily in the urine with smaller amounts in the faeces.

The possibility that dietary estrogenic isoflavones may have some therapeutic benefit in acute menopausal symptoms was suggested by the observation that Japanese women who typically have much higher dietary levels of isoflavones (mostly derived from soya) compared to women in Western countries have a reportedly lower incidence of acute menopausal syndrome symptoms such as hot flushes. This has led to somewhat speculative claims of therapeutic benefit of the isoflavones from the group daidzein, formononetin, biochanin and genistein in the treatment and/or prevention of acute menopausal syndrome symptoms (U.S. Pat. No. 5,498,631 -Gorbach et al).

Gorbach analysed urinary isoflavone excretion in Japanese subjects who consumed a traditional Japanese low-fat diet. The presence of estrogenic isoflavones in the urine of the women, men and children studied suggested to Gorbach that the isoflavones produced a therapeutic effect. The obvious flaws in this study, namely that in a diet with high isoflavone intake significant urinary out-put of isoflavones would be expected, and the huge number of biochemically active species in any diet make it impossible to ascribe biological effects to any particular component or components indicate that Gorbach's claims do not stand scrutiny. The fact that a community with a particular health profile happens to have a high dietary level (and high body levels) of a certain plant component in no way establishes cause and effect. This is only achieved through appropriately conducted clinical studies where well accepted scientific principles can be applied.

Clinical and other studies done to date in this area are highly equivocal, with no consistent effect reported. Reported studies have involved the challenge of peri-menopausal women either with whole foodstuffs (such as soyflour) containing isoflavones or with extracts of soya or other legumes, often together with other agents such as vitamins, or isoflavones together with estrogen and/or vitamins and various minerals. It is to be noted that soy does not contain the isoflavones formononetin and biochanin. Even when a positive clinical effect has been obtained, it has been with a mixture of a plurality of isoflavones, as well as a wide range of other unidentified dietary components and other biologically active components—it is known for example that other compounds present in legumes such as flavonoids (eg. quercetin, luteolin, kaempferol and lignans) also are estrogenic and it is also likely that among the other 700 or so isoflavonoids present in the Leguminosae family there are as yet unidentified isoflavonoids with estrogenic activity.

Gorbach suggests that isoflavanoids bind to estrogen receptors, exerting an estrogenic effect in menopausal women. However, it is acknowledged generally that no direct evidence exists to link the presence of isoflavones with a therapeutic effect in treatment and/or prevention of acute menopausal syndrome symptoms. But even if such a link could be inferred from the current epidemiological and clinical studies, which it can not, the question remains what, if any, therapeutic effect is the result of a collective effect of the estrogenic isoflavones—daidzein, formononetin, biochanin, genistein. All four isoflavones are estrogenic, but they have quite different estrogenic potencies. The relative estrogenicity of genistein, daidzein, formononetin, biochanin is 1.3, 0.09, 0.01, 0.07 respectively (relative to 17p-estradiol 100). Hence formononetin and biochanin have negligible estrogenic activity. On this basis, and given the relative proportions of daidzein and genistein in the blood of Japanese maintaining a typical Japanese diet, it might be inferred that genistein potentially is the most potent isoflavone as far as acute menopause syndrome symptoms are concerned.

Estrogenic isoflavones have also been identified as possible therapeutic compounds in the treatment and/or prevention of osteoporosis. Asian populations consuming large amounts of phytoestrogen-rich soybeans and vegetables appear to be protected to a greater extent than western populations from the problems associated with osteoporosis. These observations are by no means clear, and are contradicted in a number of studies.

Fujita and Fukase (Proc. Soc. Exp. Biol. Med. 200(2) 149–5, 1992) indicates that in osteoporosis analysis between Japanese and U.S. populations diet is not of particular significance, with bone mass being very similar in both populations. Instead they suggest the outcomes of osteoporosis are more likely associated with lifestyle affecting muscle development and motor control. Arjanandi et al (American Institute of Nutrition, p 161–167, 1995) indicates that any protective effects of soy on bone is associated with soy protein. Hunt et al (Am. J. Clin. Nutr., p 517–523, 1989) indicate that there is no appreciable difference in bone density between elderly menopausal omnivores, and elderly menopausal vegetarians whose diet included isoflavone rich plant materials.

Published European Patent Application No. 0135172 (Takeda, published May 27, 1985) discloses mews for-the treatment of osteoporosis by administration of 7,4-dihydroxy isoflavone (daidzein) relying on its estrogenic activity. This finding is inconsistent with the biological studies reported above. Moreover, Tobe et at (Biosci. Biotech. Biochem. 61(2) 370–371, 1997) show that daidzein stimulates bone resorption, that is bone breakdown, and would be contra-indicated for treating osteoporosis, as it would worsen an existing condition, and possibly predispose a non affected person to osteoporosis.

Against the foregoing background, the present invention is predicated upon our surprising finding that, within the framework of what was conjectured regarding the treatment/prevention of menopausal symptoms and osteoporosis, formononetin may be used to treat both menopausal symptoms and osteoporosis, and daidzein may be used in the treatment of menopausal symptoms. Our findings indicate that formononetin has pronounced clinical activity in the treatment and/or prevention of menopausal symptoms and in the treatment and/or prevention of osteoporosis as does daidzein in the treatment/prevention of menopausal symptoms. This is highly unexpected given the negligible estrogenic effect of formononetin, the bone resorption activity of daidzein and the established view that formononetin was very rapidly metabolised to daidzein in the gut.

SUMMARY OF THE INVENTION

There is provided in a first aspect of this invention a method for the treatment or prevention of menopausal symptoms or osteoporosis wherein there is administered to a subject in need of such treatment a therapeutically effective amount of the isoflavone formononetin, or a method for the treatment or prevention of menopausal symptoms wherein there is administered to a subject in need of such treatment a therapeutically effective amount of the isoflavone daidzein, the isoflavone being optionally administered with one or more pharmaceutically acceptable adjuvants, carriers and/or excipients.

In another aspect of the invention there is provided a pharmaceutical composition for the treatment or prevention of menopausal symptoms or osteoporosis wherein the said composition comprises the isoflavone formononetin or a pharmaceutical composition for the treatment of prevention of menopause wherein said composition comprises the isoflavone daidzein together with one or more pharmaceutically acceptable adjuvants, carriers and/or excipients.

In another aspect of the invention there is provided use of the isoflavone formononetin in the treatment or prevention of menopausal symptoms or osteoporosis, or use of the isoflavone daidzein in the treatment or prevention of menopausal symptoms, the isoflavone being optionally administered with one or more pharmaceutically acceptable adjuvants, carriers, and/or excipients.

In a further aspect of the invention there is provided an agent for the treatment or prevention of menopausal symptoms or osteoporosis, or an agent for the treatment or prevention of menopausal symptoms which comprises daidzein optionally in association with one or more pharmaceutically acceptable adjuvants, carriers and/or excipients.

DETAILED DESCRIPTION

Throughout this specification and the appended claims, unless the context requires otherwise, the word "comprise", or variations such as "comprises" or "comprising" or "include" or "including", will be understood to imply the inclusion of a stated element or integer or group of elements or integers but not the exclusion of any other element or integer or group of elements or integers.

The present invention provides in a first aspect a method for the treatment or prevention of menopausal symptoms or osteoporosis wherein there is administered to a subject in need of such treatment a therapeutically effective amount of the isoflavone formononetin, or a method for the treatment or prevention of menopausal symptoms wherein there is administered to a subject in need of such treatment a therapeutically effective amount of the isoflavone daidzein, the isoflavone being optionally administered with one or more pharmaceutically acceptable adjuvants, carriers and/or excipients.

It is believed that the invention described represents a substantial breakthrough in the field of treatment and/or prevention of menopausal symptoms and osteoporosis. The administration to subjects of plant extracts containing a range of isoflavones may be unpleasant in the sense that the extract may not be particularly palatable, and/or may contain a host of ill-defined compounds which may affect disadvantageous biological activity. Wilcox et al (*British Medical Journal* (1990) 301: 905) have reported increases in vaginal cell proliferation amongst post-menopausal women consuming soybean phytoestrogens for six weeks. In addition Markiewicz et al (J. Steroid Biochem. (1993) 45: 399) have shown experimentally that the soy isoflavone genistein exhibited an estrogen effect on endometrial cancer cells, that is, potentiated cancer cell growth in this cell type. Such reports raise questions about the safety of comparatively high doses of genistein. The present invention provides the treatment or prevention of menopausal symptoms and osteoporosis without any side effects caused by uncharacterised biologically active plant materials (such as coumesterols), or other disadvantageous effects.

The menopausal symptoms which may be treated according to the method of this invention are those described by Greene, J. G. and Cooke, D. J. (1980) *British Journal of Psychiatty* Volume 136, 486–491. Preferably the menopausal symptoms treated or prevented according to the present invention are hot sweats and night time sweats, more particularly hot sweats. Having said this, the method of the invention is applicable to the treatment and/or prevention of other symptoms of menopause as previously described. The isoflavone formononetin is of the formula (I):

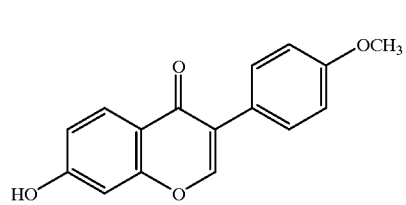

(I)

Although it was previously thought that formononetin was almost immediately metabolised (demethylated) to daidzein upon administration to a subject, the present inventors have found that formononetin persists in the blood stream for a considerable time (having a half life of generally about 20 hours).

The isoflavone daidzein is of the formula (II):

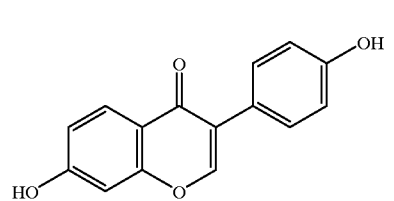

(II)

Formononetin or daidzein are preferably administered to a subject substantially unaccompanied by other isoflavones. By this is meant that any composition or preparations may contain minor amounts of other isoflavones, in the order of 10% (w/w) or less. Preferably the formononetin or daidzein represents at least 90% of isoflavone content, more preferably 95%, even more preferably 98% or more. Genistein, if present, is in amounts of about 5% or less, more preferably less than 1% (w/w) with regard to isoflavone content. It is recognised by regulatory agencies that an isoflavone content in the order of 95% of total isoflavones represents effective purity.

In the treatment of menopausal symptoms formononetin may be administered in combination with daidzein, for example from a ratio of 1:10 to 10:1.

Daidzein metabolites may be used in place of daidzein in the various embodiments of this invention. These metabolites include equol, o-desmethylangolensin (ODMA), dehydroequol, 2-dehydro-ODMA, 6-hydroxy-ODMA, dihydrodaidzein and tetra-hydrodaidzein (which collectively may be referred to hereinafter as daidzein metabolites). Accordingly, in a further aspect this invention extends to a method for the treatment or prevention of menopausal symptoms or osteoporosis wherein there is administered, to a subject in need of such treatment and/or prevention, formononetin or a daidzein metabolite, optionally administered with one or more pharmaceutically acceptable adjuvants, carriers and/or excipients. The formononetin or daidzein metabolites may be administered in a form substantially unaccompanied by other isoflavones.

Daidzein and/or formononetin compositions or preparations are administered in an amount, and under a dosage regime which gives relief to menopausal symptoms or osteoporosis. With regard to menopausal symptoms this can be readily determined by the subject who is being treated, or by their physician. Generally, it is found that prevention or therapy of menopausal symptoms and osteoporosis results from daily administration of formononetin such as from one to six times in a 24 hour period, as does the treatment or prevention of menopausal symptoms with daidzein, so as to give a daily dose of the isoflavone in an amount from about 5 mg to about 400 mg per day (this dosage range may be referred to as the "effective amount").

Formononetin and daidzein may be prepared by synthesising the compounds by conventional chemical synthetic techniques as are well known in the art, or by purification from extracts of plants of the genus Leguminosae, particularly from soy (such as from soy flour, soy hypocotyls) and clover (such as red clover, and subterranean clover) such as to form a formononetin or daidzein composition or preparation.

Compositions/preparations administered to subjects for the treating and/or prevention of, or for reducing the predispositon to, menopausal symptoms or osteoporosis may comprise in addition to the specific isoflavones previously mentioned formononetin optionally administered with one or more pharmaceutically acceptable adjuvants, carriers and/or excipients, so as to form a composition or preparation. Pharmaceutically acceptable adjuvants, carriers and/or excipients, and the like, are well known in the art, for example as described in the *Handbook of Pharmaceutical Excipients*, second edition, American Pharmaceutical Association, 1994 (incorporated herein by reference). Daidzein or formononetin may be administered in the form of tablets, capsules, powders for reconstitution, syrups, foods (such as food bars, biscuits, snack foods and other standard food forms well known in the art) or in drink formulations. Drinks may contain flavouring, buffers and the like.

In the method of this invention calcium may be co-administered (that is before at the same time or after the isoflavones previously mentioned), for example as a separate tablet, or as part of a suitable dosage form.

In a further aspect of this invention there is provided a pharmaceutical composition for the treatment or prevention of menopausal symptoms or osteoporosis wherein the said composition comprises the isoflavone formononetin or a pharmaceutical composition for the treatment or prevention of menopause wherein said composition comprises the isoflavone daidzein, together with one or more pharmaceutically acceptable adjuvants, carriers and/or excipients. As mentioned above, pharmaceutically acceptable adjuvants, carriers and/or excipients are well known in the art. Examples include compositions according to the present invention may include one or more pharmaceutically acceptable carriers. The carriers are selected so as to be acceptable in the sense of being ingredients in the composition and must not be deleterious to the patient. The carriers may be solid or a liquid, or both, and may be formulated with the extract as a unit-dose, for example a tablet, which may contain from 0.5% to 59% by weight of the active compound or up to 100% by weight to the active compound. Compositions may be prepared by any of the well known techniques of pharmacy, for example admixing the components, optionally including excipients, diluents (for example water) and auxiliaries as are well known in the pharmaceutical field.

The compositions of the invention include those suitable for oral, rectal, optical, buccal (for example sublingual), parental (for example subcutaneous, intramuscular, intradermal and intravenous) and transdermal administration. The most suitable route in any given case will depend on the nature and severity of the condition being treated and the state of the patient.

Compositions suitable for oral administration may be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the active isoflavone and one or more suitable carriers (which may contain one or more accessory ingredients as noted above). In general the compositions of the invention are prepared by uniformly and intimately admixing the isoflavone with a liquid or finely divided solid carrier, or both, and then, if necessary, shaping the resulting mixture. For example, a tablet may be prepared by comprising or moulding a powder or granules containing the extract, optionally with one or more accessory ingredients. Compressed tables may be prepared by compressing in a suitable machine, the extracts in the form of a powder or granules optionally mixed with a binder, lubricant, inert diluents, and/or surface active/dispersing agent(s). Moulded tablets may be made by moulding, in a suitable machine, the powdered compound moistened with an inert liquid binder.

Suitable carriers may be fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylceullose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients may be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules may comprise the extracts in the form of granules, for example in admixture with fillers, such as lactose, binders, such as starches, and/or glicants, such as talc or magnesium stearate, and, where appropriate, stabilisers. In soft capsules, the extract is preferably dissolved or suspended in suitable liquids, such as fatty oils, paraffin oil or liquid polyethylene glycols, to which stabilisers may also be added.

Formulations suitable for buccal (sublingual) administration include lozenges comprising the extracts in a flavoured base, usually sucrose and acacia or tragacanth; and pastilles comprising the compound in an inert base such as gelatin and glycerin or sucrose and acacia.

Formulations suitable for rectal administration are preferably presented as unit dose suppositories. These may be prepared by admixing the isoflavones with one or more conventional solid carriers, for example cocoa butter, and then shaping the resulting mixture.

Compositions may include calcium or other active agents suggested to provide some amelioration of osteoporosis or symptoms of menopause.

Pharmaceutical compositions generally comprise from about 5 mg to about 400 mg of the isofla-sone/s and may be administered one or more times per day.

In a further aspect of this invention there is provided use of the isoflavone formononetin in the treatment or prevention of menopausal symptoms or osteoporosis, or use of the isoflavone daidzein in the treatment or prevention of menopausal symptoms, the isoflavone being optionally administered with one or more pharmaceutically acceptable adjuvants, carriers, and/or excipients.

In another aspect of the invention there is provided use of formononetin, for the manufacture of a medicament for the treatment or prevention of menopausal symptoms or osteoporosis, or use of daidzein or formononetin for the manufacture of a medicament for the treatment or prevention of osteoporosis. Generally, the isoflavone is provided in the form of a medicament in association with one or more pharmaceutically adjuvants, carriers and/or excipients. Daidzein and/or formononetin may be conveniently blended as a dry powder with other components and formed into appropriate dosage forms. Such medicaments generally comprise from about 5 mg to about 400 mg of isoflavone.

According to a still further aspect of the invention there is provided an agent for the treatment or prevention of menopausal symptoms or osteoporosis, or an agent for the treatment or prevention of menopausal symptoms which comprises daidzein optionally in association with one or more pharmaceutically acceptable adjuvants, carriers and/or excipients.

Daidzein and/or formononetin may be administered in the form of a dietary product, as mentioned above, for example in a palatable food carrier such as a confectionary bar, biscuit, cereal or beverage.

The methods and compositions of the present invention do not include the use of estrogens, or components such as licorice, cholecalciferol and vitamin E. Estrogen administration has many side effects such as genital bleeding and hepatic disorders. Licorice has vasoactive activity and may exacerbate menopause symptoms or osteoporosis. Cholecalciferol and vitamin E are also disadvantageous.

The foregoing description in relation to daidzein, applies to the daidzein metabolites equol, o-desinethylangolensin (ODMA), dehydroequol, 2-dehydro-ODMA, 6-hydroxy-ODMA, dihydrodaidzein and tetra-hydrodaidzein, as well as combinations of the above species.

Hence daidzein may be replaced by one or more of these metabolites. Daidzein or formononetin may also take the form of aglycones, glycosides, malonyl or acetyl derivatives.

This invention will now be described with reference to the following non-limiting examples.

EXAMPLE 1

Peri-menopausal women with symptoms of acute menopausal syndrome including at least an average of 3 hot flush episodes per day were treated with a preparation containing a concentrated amount of daidzein, formononetin, genistein and biochanin prepared according to the method described in published Australian patent application 40523/93 (incorporated herein by reference). The preparation contained 100 mg isoflavones containing biochanin and formononetin (in the ratio of 1.8:1). Urine samples were collected from each woman at the start of the test and then again at the end of the trial and the levels of particular isoflavones in the urine (as a marker of total body isoflavone ratios) then correlated with the degree of reduction in the incidence of hot flushes per day over the course of the study. Daidzein and genistein were detected in the urine of all test subjects but the levels were highly variable, ranging from barely detectable to relatively high. Formononetin and biochanin levels ranged between undetectable and significant. Genistein levels showed no correlation with therapeutic response; daidzein levels correlated well with therapeutic response indicating potential therapeutic utility of daidzein and formononetin.

EXAMPLE 2

Daidzein substantially free of other isoflavones was prepared from soy by the following method. 1 kg of defatted soyflour (readily available from many commercial sources) was added to 10 L of water containing 50 g of glucan hydrolase enzyme (Bio-Feed Beta CT, Novo Nordisk, Denmark). To this suspension 5 L of ethyl acetate is then added. This mixture is mixed vigorously using a high pressure pump for 3 hours so that it forms an emulsion. This mixing ensures effective contact between the aqueous phase and the miscelles of ethyl acetate so that the enzymatically hydrolysed aglucone forms of the isoflavones move from the aqueous to the organic solvent phase. The three phases (soyflour, aqueous, ethyl acetate) are separated by centrifugation in a swing bucket centrifuge at 2000 g for 30 minutes. The upper phase comprising ethyl acetate is aspirated, 200 ml of water added, and then placed into a rotary evaporator at 75° C. under a weak vacuum. Upon removal of the ethyl acetate, the residual aqueous phase containing the isoflavones is extracted once with 500 ml of hexane to remove oils and fats, and then twice with 500 ml of octanol which selectively removes genistein. The aqueous phase then was taken to dryness overnight in an oven at 80° C. This material was shown by high pressure liquid chromatographic analysis to comprise 65% isoflavones comprising daidzein (95%): genistein(5%): formononetin(0%): biochanin(0%). This material was mixed with standard carriers/excipients and tableted to give 500 mg tablets containing 25 mg daidzein. In this particular example, the daidzein was tableted with equivalent (wiw) amounts of microcrystalline cellulose, calcium hydrogen phosphate, magnesium stearate and anhydrous colloidal silica.

Formononetin substantially free of other isoflavones was prepared from clover by enzyme/solvent as above. Formononetin was recovered as a purity level greater than 95% by chromatographic analysis or by HPLC.

EXAMPLE 3

The dried end product of the first part of Example 2 above can be used to further concentrate genistein or daidzein with/without. 3 kg of this material is mixed with 1000 L of an organic solvent such as acetone, chloroform or octanone, but preferably acetone for reasons of safety and cost. Each of these 3 solvents has been shown by the inventors to have high affinity for genistein but not daidzein. The mixture is stirred continuously at room temperature for between 1–24 hours but preferably 2 hours during which time a large amount (approximately 75%) of the genistein transfers into the solvent phase. The mixture is allowed to settle for about 2 hours, the solvent is separated from the residue (Sample 2) and transferred to a still for evaporation. Sample 2 material preferably is extracted with acetone a further 1–5 times (preferably 4 times). This material typically contains 76% daidzein, 1% genistein, 0.5% glycetein, with the remainder comprising residual lipid soluble material such as short chain fatty acids. On a w/w basis compared with the other isoflavones, this preparation contains 98% (w/w) daidzein. Daidzein may be purified to 95% (w/w) of total material or more purity by preparative purification regimens such as preparative HPLC. A daidzein preparation according to this example is tabletted with conventional inert excipients according to Example 3 to give a 200 mg tablet containing 50 mg daidzein.

EXAMPLE 4

A group of 36 post-menopausal women experiencing menopausal symptoms were treated with a composition containing either 15 mg daidzein or 60 mg daidzein administered on a daily basis for 3 months. Compared to a placebo control group there was a significant decrease in the Greene Score for menopausal symptoms which corresponds to treatment/amelioration of menopausal symptoms (such as hot flushes). The urinary profile of these subjects demonstrated the therapeutic effectiveness of daidzein as against other isoflavones.

In a similar study the same dosage levels of formononetin again gave a significant decrease in Greene Score for menopausal symptoms as for daidzein.

EXAMPLE 5

A pharmacokinetic study involving 16 human patients aged between 18 and 40 was conducted, to determine the pharmacokinetics of formononetin following oral administration. Each patient was orally administered 9.3 mg of formononetin with 200 ml of purified water and maintained a low isoflavone diet for one week prior to, and during the study. Blood samples were taken at 0, 0.25, 0.5, 0.75, 1.0, 1.5, 2.0, 2.5, 3, 4, 5, 6, 8, 10 and 12 and 24 hours post administration, and analysed for formononetin concentration.

An analysis of formononetin concentrations (ng/ml) against time demonstrated that contrary to previous opinion, unmetabolised formononetin persists in the blood stream for considerable 30 time following administration (having a half life of about 20 hours).

EXAMPLE 6

15 post-menopausal women who are experiencing menopausal systems are each administered 60 mg formononetin daily for three months. Relative to a control group the treatment group show a significant decrease in Greene Score for menopausal symptoms.

A similar study involving 10 post-menopausal women in a high risk group for osteoporosis were also administered 60 mg formononetin daily for three months. Preliminary results indicate protection against osteoporosis in the treatment group when measured by bone density and bone turnover markers were measured.

EXAMPLE 7

The second study (double-blind, placebo-controlled) involved a six month study of the effects of phytoestrogen formononetin on bone resorption markers in twenty post-menopausal women. The aim of the study was to evaluate the efficacy of a defined daily quantity of isoflavone at 25 mg, 50 mg or 75 mg on bone resorption makers in post menopausal women and compare these to normal controls The effects of isoflavones on endometrial thickness, circulatory lipids and coagulation factors were also evaluated. Subjects were also given supplemental calcium in a dose of 1200 mg per day.

Bone density measurements using a bone densitometer were made at three sites of the forearm at 0.3 and 6 months and showed significant improvement in bone density. Bone markers for osteocalcin, deoxy pyridinoline crosslinks, N-terminal collagen crosslinks, calcium and other markers showed a similar improvement in bone resorption and turnover.

It is to be recognized that the present invention has been described by way of example only, and that various modifications and/or alterations which would be obvious to a person skilled in the art, on the basis of the teaching herein, can be made thereto without departing from the intended scope or spirit of the invention.

What is claimed is:

1. A method for the treatment or prevention of osteoporosis comprising administering to a subject in need of such treatment a therapeutically effective amount of the isoflavono formononetin optionally administered with one or more pharmaceutically acceptable adjuvants, carriers and/or excipients.

2. A method according to claim 1, wherein formononetin is present in an amount of about 90% (w/w) as against any other isoflavones.

3. A method according to claim 1, wherein the isoflavone is administered at least once per day.

4. A method according to claim 1, wherein the isoflavone is administered in an amount from about 5 mg/day through to about 400 mg/day.

5. A method according to claim 1, wherein the isoflavone is administered from 1 to 6 times in a 24 hour period so as to give a daily dosage of from about 5 to about 400 mg.

6. A method for the treatment or prevention of osteoporosis comprising administering a therapeutically effective amount of a combination of formononetin and daidzein to a patient in need of such treatment.

7. A method according to claim 6, wherein daidzein is a daidzein metabolite selected from equol, o-desmethylangolensin dehydroequol, 2-dehydro-o-desmethylangolensin, 6-hydroxy-o-desmethyl-olensin, dihydrodaidzein and tetra-hydrodaidzein.

8. A composition for the treatment or prevention of osteoporosis wherein the said composition comprises the isoflavone formononetin together with one or more pharmaceutically acceptable adjuvants, carriers and/or excipients.

9. A composition for the treatment or prevention of osteoporosis wherein the said composition includes a combination of formononetin and daidzein.

10. A composition according to claim 9, which comprises from 5 to 400 mg of isoflavones.

11. A composition according to claim 9, wherein daidzein is a daidzein metabolite selected from equol, o-desmethylangolensin, dehydroequol, 2-dehydro-o-desmethylangolensin, 6-hydroxy-o-desmethylangolensin, dihydrodaidzein and tetra-hydrodaidzein.

12. A method according to claim 6, wherein the isoflavones are in the aglycone, glycoside, malonyl or acetyl form.

13. A composition according to claim 9, wherein the isoflavones are in the aglycone, glycoside, malonyl or acetyl form.

14. A method according to claim 6, wherein formononetin is administered in combination with daidzein in a ratio from 10:1 to 1:10 (w/w).

15. A composition according to claim 9, which comprises formononetin and daidzein in a ratio from 10:1 to 1:10 (w/w).

16. A composition according to claim 8, wherein formononetin is present in an amount of about 90% (w/w) as against any other isoflavones.

17. A method according to claim 6, wherein the isoflavones are administered at least once per day.

18. A method according to claim 6, wherein the isoflavones are administered in an amount from about 5 mg/day to about 400 mg/day.

19. A method according to claim 1, wherein formononetin is derived from a plant.

* * * * *